(12) United States Patent
Maejima

(10) Patent No.: US 6,683,266 B2
(45) Date of Patent: Jan. 27, 2004

(54) APPARATUS FOR INSPECTING GEL COVERING SEED

(75) Inventor: Takamichi Maejima, Hyogo (JP)

(73) Assignee: Agritecno Yazaki Co., Ltd., Hyogo (JP)

( * ) Notice: Subject to any disclaimer, the term of this patent is extended or adjusted under 35 U.S.C. 154(b) by 0 days.

(21) Appl. No.: 10/123,994

(22) Filed: Apr. 16, 2002

(65) Prior Publication Data

US 2002/0175178 A1 Nov. 28, 2002

(30) Foreign Application Priority Data

Apr. 23, 2001 (JP) .................................... 2001-124027

(51) Int. Cl.[7] ................................................ B07C 5/00
(52) U.S. Cl. ...................................... 209/587; 209/588
(58) Field of Search ............................... 209/588, 587, 209/576, 577, 539, 623, 639, 644, 922, 932; 198/381, 393, 493

(56) References Cited

U.S. PATENT DOCUMENTS

| | | | | |
|---|---|---|---|---|
| 3,197,647 A | * | 7/1965 | Fraenkel | 250/225 |
| 3,581,888 A | * | 6/1971 | Kelly et al. | 209/565 |
| 3,880,289 A | * | 4/1975 | Gray | 209/587 |
| 5,135,114 A | * | 8/1992 | Satake et al. | 209/558 |
| 5,201,576 A | * | 4/1993 | Squyres | 362/3 |
| 5,352,888 A | * | 10/1994 | Childress | 250/223 R |
| 5,713,473 A | * | 2/1998 | Satake et al. | 209/580 |
| 5,917,927 A | * | 6/1999 | Satake et al. | 382/110 |
| 5,973,286 A | * | 10/1999 | Wan | 209/582 |
| 5,986,230 A | * | 11/1999 | Novak et al. | 209/579 |
| 6,078,018 A | * | 6/2000 | Davis et al. | 209/580 |

FOREIGN PATENT DOCUMENTS

| | | | |
|---|---|---|---|
| AU | WO 89 01832 A1 | * | 3/1989 |
| JP | 8-27237 | | 3/1996 |
| JP | 09 122606 | | 5/1997 |
| JP | 09 225413 | | 9/1997 |
| JP | 09 239330 | | 9/1997 |

* cited by examiner

Primary Examiner—Donald P. Walsh
Assistant Examiner—Joseph C Rodriguez
(74) Attorney, Agent, or Firm—Knobbe, Martens, Olson & Bear LLP

(57) ABSTRACT

A gel covering seed inspection apparatus 1 of the present invention comprises a feeder 3 in which the gel covering seed 19 is accumulated, a delivery device 4 which successively lets out a predetermined number of the gel covering seed supplied thereto at a constant rate from the feeder, a transport device 5 which conveys the gel covering seed 19 let out by the delivery device in a line, a discrimination device 6 which judges the acceptance or rejection on the midway of conveyance of the gel covering seed 19 by the transport device 5, a defective product reject device 7 which rejects the gel covering seed 19 judged to be a defective product, and an accepted product extractor 9 which takes out the gel covering seed 19 judged to be an accepted product to an accepted product box 10. The discrimination device 6 is provided with a camera 61 and a luminaire 62 which are arranged face to face on both sides of the transport device 5. The discrimination device 6 inspects the seed by taking a permeation reflection of the gel covering seed 19 with the camera 61 by the light that the luminaire 62 emits, and judges the acceptance or rejection of the gel covering seed 19 based on the permeation reflection.

11 Claims, 17 Drawing Sheets

APPARATUS FOR INSPECTING GEL COVERING SEED

BACKGROUND OF THE INVENTION

1. Field of the Invention

The present invention relates to an apparatus for inspecting gel covering seed, which convey every one gel covering seed from a hopper, investigate whether the seed of a predetermined number is contained in gel, and sort out to an accepted product and a defective product.

2. Related Art

The Japanese Patent Publication Hei.8-27237 describes a well-known conventional technique for producing gel covering seeds, i.e., seeds coated with gel, investigating whether a seed is contained in the gel or not, and whether seeds more than a predetermined number are contained in the gel, wherein the color of the seed in the gel covering seed under conveyance is detected by a collar sensor, and judge whether the ripple of the color wavelength approximates as compared with a predetermined ripple pattern.

However, in the technique, the setting of values before an inspection is difficult, since it is necessary to manage the conveyance speed of a gel covering seed strictly, to determine the color of a seed before an inspection, and to also establish the pattern of a seed. Therefore, if the color of a seed differs from the predetermined color, the gel covering seed will be judged to be defective products. Moreover, judgment of an accepted product or a defective product varies by the degree of the illumination light from the outside.

SUMMARY OF THE INVENTION

An object of the present invention is to provide an apparatus which can distinguish the existence of a seed easily with a cheap device, without not being influenced from surrounding illumination and not detecting the color of the seed in a gel covering seed, while establishing a conveyance form which certainly sorts out each gel covering seed to either an accepted product or a defective product.

In order to attain this object, a gel covering seed inspection apparatus comprises a feeder in which the gel covering seed is accumulated, a delivery device which successively lets out a predetermined number (in this embodiment, one) of the gel covering seed supplied thereto at a constant rate from the feeder, a transport device which conveys the gel covering seed let out by the delivery device in a single line, a discrimination device which judges acceptance or rejection of the gel covering seed on the midway of conveyance by the transport device, a defective product reject device which reject the gel covering seed judged to be a defective product, and an accepted product extractor which takes out an accepted product to an accepted product receipt box. In such composition, a predetermined number of the gel covering seed let out from the delivery device is continuously conveyed in a single line to the discrimination device. This conveyance form contributes to a certain judgment on the acceptance or rejection of a gel covering seed by the discrimination device, and to offer the gel covering seed inspection apparatus which has high inspection accuracy and inspection efficiency.

In the inspection apparatus of such the invention, the discrimination device is provided with a camera and a luminaire arranged face to face on both sides of the transport device, and inspects the seed in gel by taking the permeation reflection of the gel covering seed with the camera by the light that the luminaire emits. Thus, since the object to be detected is not the color of the seed in a gel covering seed but the shadow of the seed which appears in the permeation reflection, the uncertainty of a judgment produced by the variation in the judgment level of color is cancelable. Therefore, acceptance or rejection judgment of a gel covering seed is made to be easy and sure, and since it is not necessary to use the distinction means of color etc., the discrimination device itself can be composed cheaply.

The discrimination device carries out calculation of the area of the shadow of the seed in the gel covering seed which appears in the permeation reflection taken with this camera, and the acceptance or rejection of a gel covering seed is judged by comparing the calculated area with the predetermined area. In comparison with the conventional discrimination means based on color which requires the complicated means of detection of the color wavelength in a reflection, the present discrimination device, which merely calculates the area of the shadow of the seed that appears in a permeation reflection, can be simple and cheap. Furthermore, because the predetermined area is established so that the seed to be inspected may correspond to the size of an accepted product, it can flexibly respond to alteration of the kind of gel covering seed to be inspect and so on.

Also, in the discrimination device, the perimeter of the luminaire and of the photography range with a camera is covered with an enclosure. Thus, light, such as the illumination from the outside and daylight, does not shine into the photography range, and discrimination accuracy can be improved because the originating incorrect detection by this light is prevented.

In addition, the inside of the enclosure may be black, therefore it can prevent that the light from a luminaire, the light which entered from the outside reflect irregularly, and a white minute seed etc. is certainly detectable.

Furthermore, the discrimination device may be provided with two cameras arranged in a rectangular location, and those cameras may be arranged so that the photography direction of those cameras and the conveyance direction of a gel covering seed may intersect perpendicularly. Thus, even if the state that the seeds in gel overlap is taken with one camera, the state that the seeds do not overlap can be taken with the other camera, so the number of the seeds in gel can be detected certainly.

Furthermore, the accepted product extractor comprises a cylinder member and a rotation driver. The cylinder member is provided in an end portion thereof with an entrance port for accepted products. The cylinder member is provided in the peripheral surface thereof with an inside-and-outside penetrating slot elongated in parallel to the axial center thereof. The cylinder member is arranged in up-and-down slant so that the entrance slot turns to the upper part, and the cylinder member ejects the accepted product introduced from the entrance slot through the long hole while revolving with the rotation driver. Therefore, from the long hole of the cylinder member, the accepted product comes to be ejected in the uniform state in the direction of an axial center of the cylinder member, so that the failure by press of the gel covering seeds, which tends to be generated when a gel covering seed is unevenly distributed, can be inhibited.

These, other and further objects, features and advantages of the invention will appear more fully from the following description.

DETAILED DESCRIPTION OF THE PREFERRED EMBODIMENT

A gel covering seed inspection apparatus of the present invention explained below may inspect other things as well as gel covering seed.

Figure 1:
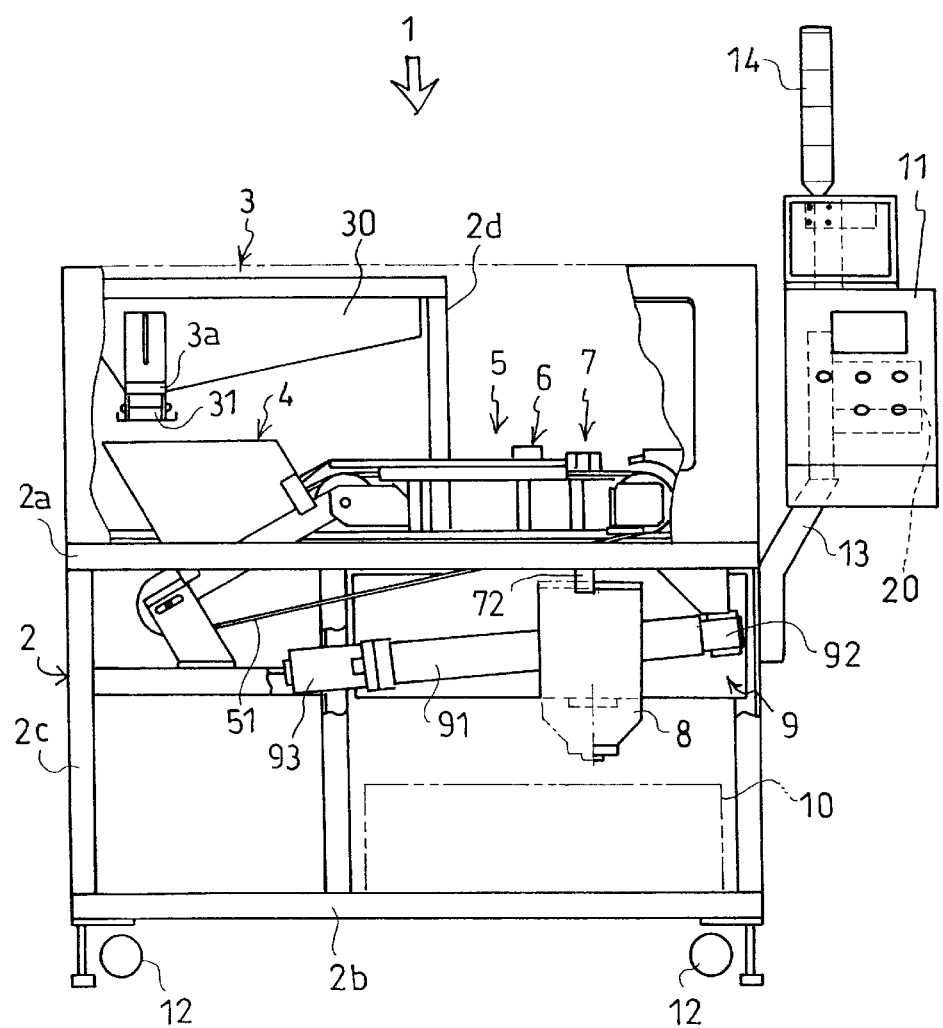
FIG. 1 is a front view of an inspection apparatus of the present invention.
Figure 2:
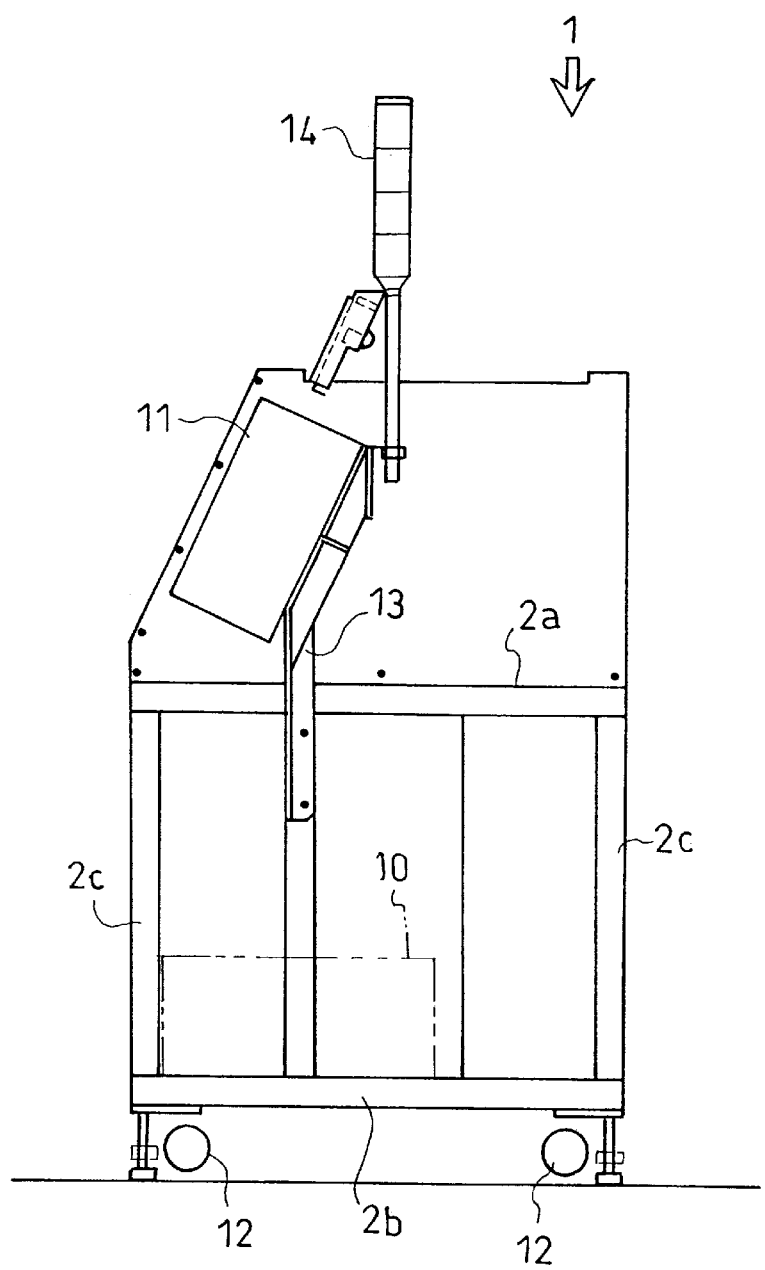
FIG. 2 is a side view of the same.

The whole construction of the inspection apparatus of the present invent ion will be explained in accordance with FIGS. 1 and 2.

An inspection apparatus 1 comprises a feeder 3 in which the gel covering seed 19 (refer to FIG. 5 etc.) is accumulated, a delivery device 4 which successively lets out a predetermined number (in this embodiment, one) of gel covering seed 19 supplied thereto at a constant rate from the feeder 3, a transport device 5 which conveys the gel covering seed let out by the delivery device 4 in a single line, a discrimination device 6 which judges either acceptance or rejection about each gel covering seed 19 on the midway of the conveyance by the transport device 5, a defective product reject device 7 which rejects the gel covering seed 19 judged to be defective products, an accepted product extractor 9 which takes out accepted products to an accepted product box 10, and a frame 2 that supports these devices.

The above-mentioned frame 2 comprises an upper frame portion 2a and a lower frame portion 2b, which are assembled by stanchions 2c in the shape of a frame. Casters 12, which make a movement of the frame 2 easy, are provided on the undersurface of the lower frame portion 2b. Further, a pair of feeder frames 2d are provided above the leftward of the upper frame portion 2a, and the feeder 3 is supported between the upper frame portion 2a and the feeder frames 2d. An exhaust port 3a is provided in the front lower part of the feeder 3.

Moreover, on the frame portion 2a, the delivery device 4, the transport device 5, the discrimination device 6, and the defective product reject device 7 are attached.

This delivery device 4 is arranged just below the feeder 3, that is, on the left hand side front part of the upper frame portion 2a. An inlet port for gel covering seed 19 is open at the upper end of the delivery device 4 so as to face the exhaust port 3a of the feeder 3, thereby receiving the gel covering seed 19 ejected from the exhaust port 3a of the feeder 3. The delivery device 4 allows an endless conveyer belt 51 of the transport device 5 to pass therethrough so as to let out the gel covering seed 19 one after another onto the conveyor belt 51, so that the transport device 5 conveys the gel covering seed 19 arranged in a line on the conveyor belt 51.

The conveyor belt 51 of the transport device 5 is wound so as to straddle the upper frame portion 2a up and down. The upper portion of this conveyor belt 51 passes the delivery device 4 in the above-mentioned manner, receives the gel covering seed 19 let out one and one from the delivery device 4 so as to arrange them in a line thereon, and conveys the gel covering seed 19 to the right hand side.

The discrimination device 6 and the defective-product reject device 7 are arranged so as to face the downstream portion of the conveyor belt 51.

The discrimination device 6 is provided with a camera 61. The camera 61 is arranged on one side of (in front or rear of) the transport device 5 (conveyor belt 51), so that the photography direction of the camera 61 and the conveyance direction of gel covering seed 19 may intersect perpendicularly. Furthermore, this discrimination device 6 processes the permeation reflection of each gel covering seed 19 under conveyance taken with the camera 61, and discriminates whether one seed is contained in each gel coat.

The defective product reject device 7 is arranged at the downstream of the discrimination device 6 in the conveyance direction of the gel covering seed 19 by the transport device 5. The defective product reject device 7 is provided with an air nozzle 71 arranged at one side of the transport device 5 and a chute 72 arranged at the other side of the transport device 5. The air nozzle 71 and the chute 72 are arranged face to face. If either the gel coat which does not contain the seed or the gel covering seed in the state where two or more grains of seeds were covered with the gel coat (it is named a "defective product" generically) is detected by this discrimination device 6, the defective product is blown away into the chute 72 by the compressed air breathed out from the air nozzle 71 at the time of its reaching a defective product reject device 7. Then, the defective product is guided by this chute 72, and is received by the defective-product receipt box 8 arranged below the chute 72.

The accepted product extractor 9 is arranged under the transport device 5, and the accepted product receipt box 10 is laid on the lower frame portion 2b below the transport device 5. The accepted product extractor 9 is provided with an inclined distribution cylinder 91, which is rotated by a motor 93. An entrance port 92 is formed in one higher end of the distribution cylinder 91 so as to be arranged just below the termination of the conveyor belt 51 of the transport device 5. The other lower end of the distribution cylinder 91 is arranged under the delivery device 4. In the peripheral surface of the distribution cylinder 91, a slot 91a is extended to the longitudinal direction (the direction of an axial center) of the distribution cylinder member 91.

Thus, the gel covering seed 19 falls from the termination of the transport device 5, enters the revolving distribution cylinder 91 through the entrance port 92, disperses inside the distribution cylinder 91 while rolling along the slant face of the distribution cylinder 91, and falls from the slot 91a. Then the gel covering seed 19 is received in the accepted product receipt box 10.

A control box 11 for controlling drive of the conveyor belt 51, rotation of the distribution cylinder 91, etc. is fixed to the upper part of the support frame 13 protruding upwardly rightward from the right-hand side of the frame 2. In the front face of the control box 11, a display panel and a console panel are formed, and at the upper part of the control box 11, an alarm lamp 14 is arranged.

Figure 3:
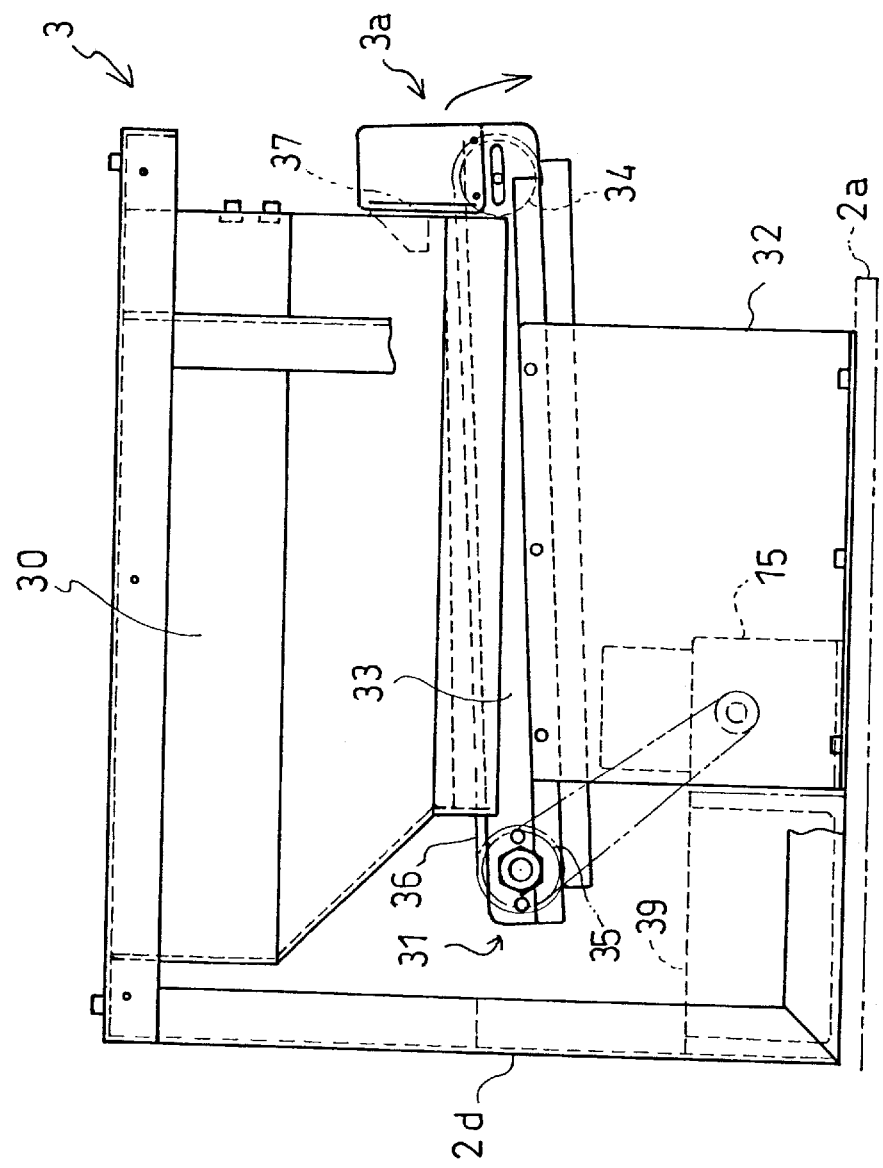
FIG. 3 is a side view of a feeder.
Figure 4:
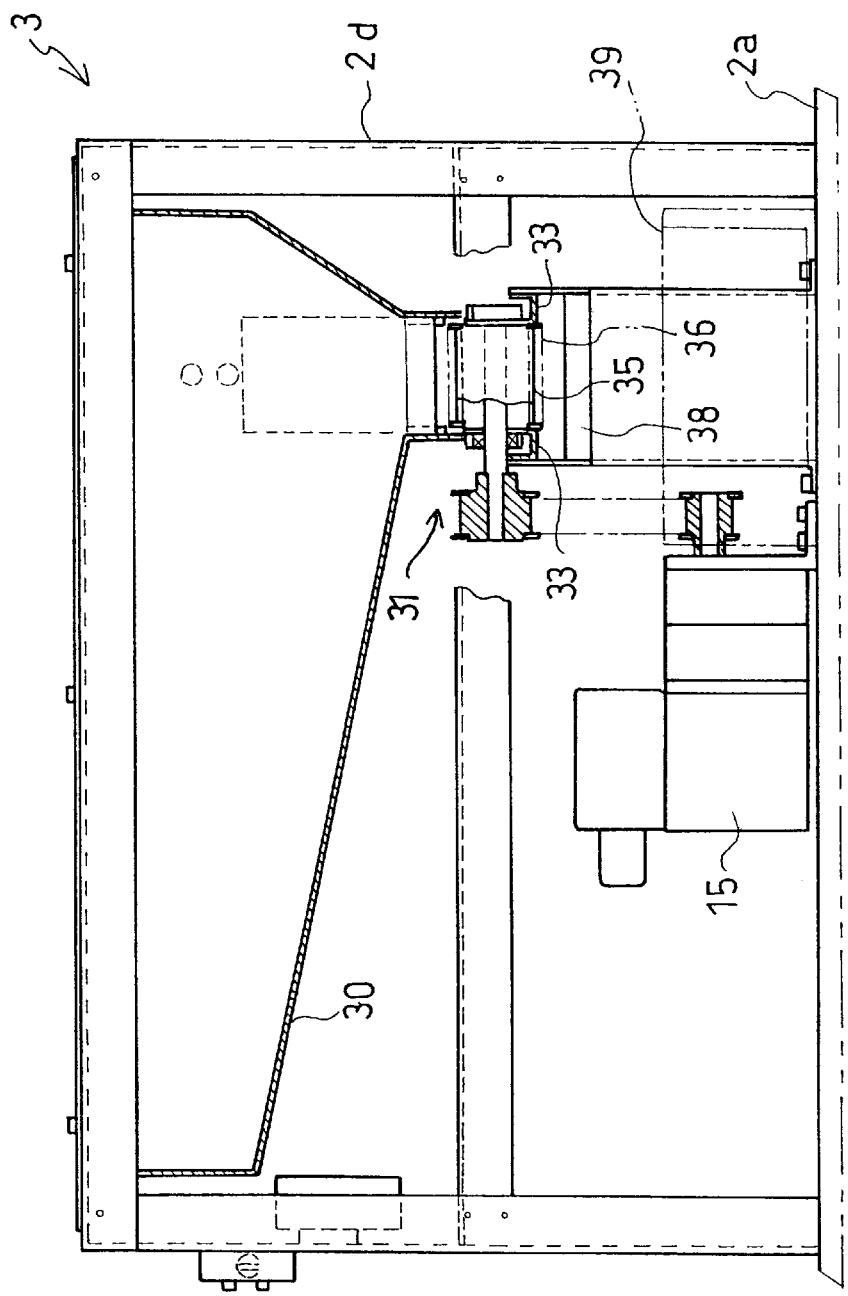
FIG. 4 is a rear view partly in section of the same.

Next, the construction of each of the devices in this inspection apparatus 1 will be detailed. First, the construction of the feeder 3 will be explained in full detail in accordance with FIGS. 3 and 4.

The feeder 3 comprises a hopper 30, which receives the gel covering seed 19 to be inspected, and an ejection conveyer 31, which ejects the gel covering seed 19 received by the hopper 30 to the delivery device 4. The hopper 30 is fixed to the upper portions of the feeder frames 2d. Under the hopper 30, the ejection conveyer 31 is fixed on a feeder stand 32 erected on the upper frame portion 2a. The front view of the hopper 30 shows the shape of a funnel with a narrow lower portion. A fall hole is formed in the left portion of the lower end of the hopper 30 so as to be extended in the fro-and-rear direction of the inspection apparatus 1. The ejection conveyer 31 is arranged in the fro-and-rear direction so as to face the fall hole at the lower end of the hopper 30. Therefore, the gel covering seed 19 which fall from the fall hole of the hopper 30 are collected on the ejection conveyer 31, and are conveyed by the ejection conveyer 31.

The construction of the ejection conveyer 31 will be explained.

The feeder stand 32 is erected on the upper frame portion 2a. A couple of left and right belt frames 33 are fixed to the upper end of the feeder stand 32 and to the lower end of the hopper 30.

A follower pulley 34 is rotatably supported between the front ends of the left and right belt frames 33. A drive pulley 35 is rotatably supported between the rear ends of the left and right belt frames 33. A conveyor belt 36 is interposed between the drive pulley 35 and the follower pulley 34. The gel covering seed 19 are conveyed from the back end to the front end of the conveyor belt 36. The front end of the conveyor belt 36 projects forward from the front surface of the hopper 30. A shutter 37 is attached to the front surface of the lower end of the hopper 30 so as to enable its vertical position to be adjusted, thereby adjusting the discharge amount of the gel covering seed 19 from the front end of the conveyor belt 36. Incidentally, an air nozzle may be arranged above the front end of the conveyor belt 36 so as to blow off the gel covering seed 19 away from the front end of the conveyor belt 36, thereby surely dropping the gel covering seed 19.

In the upper portion of the feeder stand 32, a trough 38 is arranged under the conveyor belt 36. The trough 38 and ejection conveyer 31 are inclined downwardly rearward. A drain box 39 is arranged on the upper frame portion 2a below the rear end of the trough 38. Water that has washed the gel covering seed 19 falling along the trough 38 is collected into the drain box 39.

Furthermore, a drive shaft of the drive pulley 35 is interlockingly connected to an output shaft of a drive motor 15 fixed on the upper frame portion 2a through a pulley, a belt, etc. The drive motor 15 is electrically connected to a controller 20 in the control box 11.

In the feeder 3 of the above-mentioned construction, the gel covering seed 19 are previously filled up in the hopper 30. By driving of the drive motor 15 actuated by control of the controller 20, the gel covering seed 19 naturally fall to the fall hole of the hopper 30, ride on the conveyor belt 36 so as to be carried, and then fall from the front end of the conveyor belt 36 into a later-discussed delivery hopper 40 of the delivery device 4. In addition, the shutter 37 limits the amount of the gel covering seed 19 per unit time discharged from the conveyor belt 36 according to the capacity and delivery rate of the delivery hopper 40.

Figure 5:
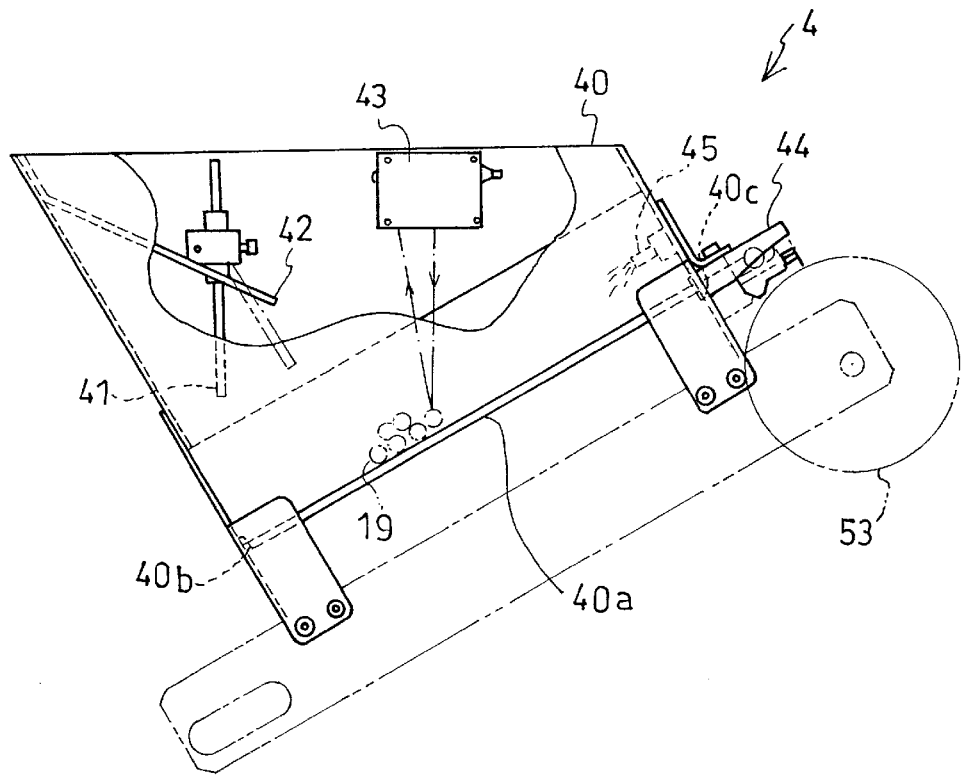
FIG. 5 is a partially cutaway front view of a delivery device.
Figure 6:
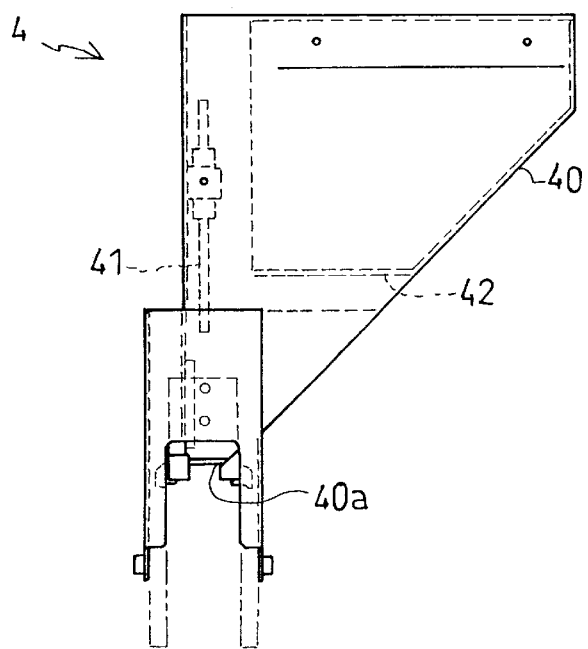
FIG. 6 is a side view of the same.

Next, the construction of the delivery device 4 will be explained in accordance with FIGS. 5 and 6.

The delivery device 4 is provided with the delivery hopper 40, which always accumulates a constant amount of the gel covering seed 19 therein. The delivery hopper 40 is composed so that the accumulated gel covering seed 19 may let out one after another to the transport device 5 arranged from the lower part to the lateral side of the delivery hopper 40.

The front view of the delivery hopper 40 is triangular, and the sectional side view thereof is V-like shaped. That is, the delivery hopper 40 substantially looks like a vertically reversed triangular pyramid. The delivery hopper 40 has a top opening and a tight bottom 40b. Through the top opening, the gel covering seed 19 falling from the feeder 3 is supplied into the delivery hopper 40. A long opening 40a is bored in a slant portion of the delivery hopper 40 extended upwardly rightward (along the conveyance direction) from the tight bottom 40b. The upstream region of the conveyor belt 51 of the transport device 5 passes through the inside of the opening 40a, so that the gel covering seed 19 in the delivery hopper 40 roll to fall onto the conveyor belt 51 arranged in the opening 40a.

Above the tight bottom 40b, an air nozzle 41 and a guide plate 42 are arranged in the delivery hopper 40. The guide plate 42 guides the gel covering seed 19 falling from the feeder 3 forward onto the conveyor belt 51 in the opening 40a. The air nozzle 41 blows air toward the tight bottom 40b so as to stir the gel covering seed collected in the delivery hopper 40, thereby preventing the gel covering seed 19 from adhering to one another so as to form bridges.

In the delivery hopper 40, a distance sensor 43 composed of a photo switch is arranged above the halfway portion of the bottom slant face in which the opening 40a is located, and electrically connected to the controller 20. The distance sensor 43 detects the height of level of gel covering seeds 19 collected in the delivery hopper 40.

When there are too many gel covering seeds 19 supplied from the feeder 3 and the top level thereof becomes higher than the predetermined height, it becomes easy to generate the bridge of the gel covering seed 19, and it becomes impossible for the delivery device 4 to let out one grain of the gel covering seed 19 at a time to the transport device 5. Thus, if it is detected by the distance sensor 43 that the level of the gel covering seed 19 collected in the delivery hopper 40 is higher than the predetermined height, the drive of the drive motor 15 is stopped by control of the controller 20 so as to stop the drive of the ejection conveyer 31 in the feeder 3, thereby suspending the feed of the gel covering seed 19 from the feeder 3 to the delivery device 4.

If the level of the gel covering seed 19 in the delivery hopper 40 becomes lower than the predetermined height, the gel covering seed 19 run short so that it becomes easy to generate lack of the gel covering seed 19 conveyed by the transport device 5. Thus, the drive motor 15 is operated to make the feeder 3 supply the gel covering seed 19 into the delivery hopper 40.

The delivery hopper 40 is tapered down to the tight bottom 40b so as to serve as a portion in which the gel covering seed 19 are gathered (hereinafter, the portion is referred to as "a seed accumulation"). The conveyor belt 51 formed thereon with a series of plural detent recesses 51b (discussed later) is moved upwardly slantwise for conveyance of the gel covering seed along the seed accumulation, so that the gel covering seed 19 in the seed accumulation are inserted one and one into the respective detent recesses 51b and conveyed by the conveyor belt 51. The level of gel covering seed 19 accumulated in the delivery hopper 40 is held at a constant height so as to prevent shortage and excess of gel covering seed 19 therein. Therefore, on the conveyor belt 51, the lack of gel covering seed 19 because of the shortage and the generation of lumps of gel covering seed 19 because of the excess are avoided.

In the delivery hopper 40, the upper end of the opening 40a, that is, the conveyance termination portion of the conveyor belt 51 in the opening 40a serves as an exhaust port 40c, which is covered with an enclosure 44 from above. In the exhaust port 40c, the spacing between the enclosure 44 and the conveyor belt 51 is established smaller than the diameter of each gel covering seed 19, while allowing the gel covering seed 51 inserted in each detent recess 51b on the conveyor belt 51 to pass therethrough. Therefore, the gel covering seed 19 are let out from the exhaust port 40c and laid one after another in a line on the conveyor belt 51.

An air nozzle 45 is arranged above the exhaust port 40c so as to blow air toward the tight bottom 40b along the conveyor belt 51 in the delivery hopper 40. By the air nozzle 45 blowing the air oppositely to the conveyance direction, the excessive gel covering seed 19 riding on the conveyor belt 51 without being inserted in the respective detent recesses 51b are blown away to the tight bottom 40b, and return to the seed accumulation.

The flow of the gel covering seed 19 in the delivery device 4 of the above construction will be summarized. The gel covering seed 19 falling from the ejection conveyer 31 of the above-mentioned feeder 3 are guided by the guide plate 42 so as to fall onto the level surface of the seed accumulation in the delivery hopper 40. The gel covering seed 19 in the seed accumulation are stirred by the air blown from the air nozzle 41, thereby being prevented from adhering one another so as to form bridges. The conveyor belt 51 passes upwardly slantwise along the stirred seed accumulation. During this passage, each one-grain of the gel covering seed 19 is inserted into each detent recess 51b on the conveyor belt 51, and conveyed with the conveyor belt 51 upwardly slantwise. On reaching the vicinity of the exhaust port 40c, the excessive gel covering seed riding on the conveyor belt 51 are blown away by the air from the air nozzle 45 to the seed accumulation on the side of the tight bottom 40b, so that only the gel covering seed 19 inserted in the detent recess 51b are taken out from the exhaust port 40c of the delivery device 4.

Incidentally, when the gel covering seed 19 are small, the gel covering seed 19 riding on the conveyor belt 51 between two gel covering seed 19 inserted in adjoining detent recesses 51b may be unable to be eliminated only with the air blown from the air nozzle 45. In such a case, as shown in FIG. 7, the conveyor belt 51 may be penetrated inside-and-outside by a plurality of air blowholes 51a arranged at regular intervals in a line or at appropriate positions around the respective detent recesses 51b, so that the air blown out through the air blowholes 51a may prevent the gel covering seed 19 from between the adjoining detent recesses 51b.

In order to apply air to the air blowholes 51a, a manifold 46a is provided below the opening 40a, that is, formed in a delivery rail 46 for upwardly supporting and guiding the conveyor belt 51. The manifold 46a is extended to some degree from the lower part of the exhaust port 40c toward the tight bottom 40b. Preferably, the end of the manifold 46a toward the tight bottom 40b corresponds to the position where the gel covering seed 19 get out of the seed accumulation.

When small gel covering seed 19 are gathered in the delivery hopper 40, they are very lightweight and include a lot of moisture, thereby being easy to adhere one another in the delivery hopper 40 so as to form bridges. Besides, if a considerably great amount of gel covering seed 19 are blown back by the air nozzle 41 in association with the position through which the gel covering seed 19 are thrown from the feeder 3 into the delivery hopper 40 or another determinant, there is a possibility that the blown-back gel covering seed 19 may dry.

Figure 7:
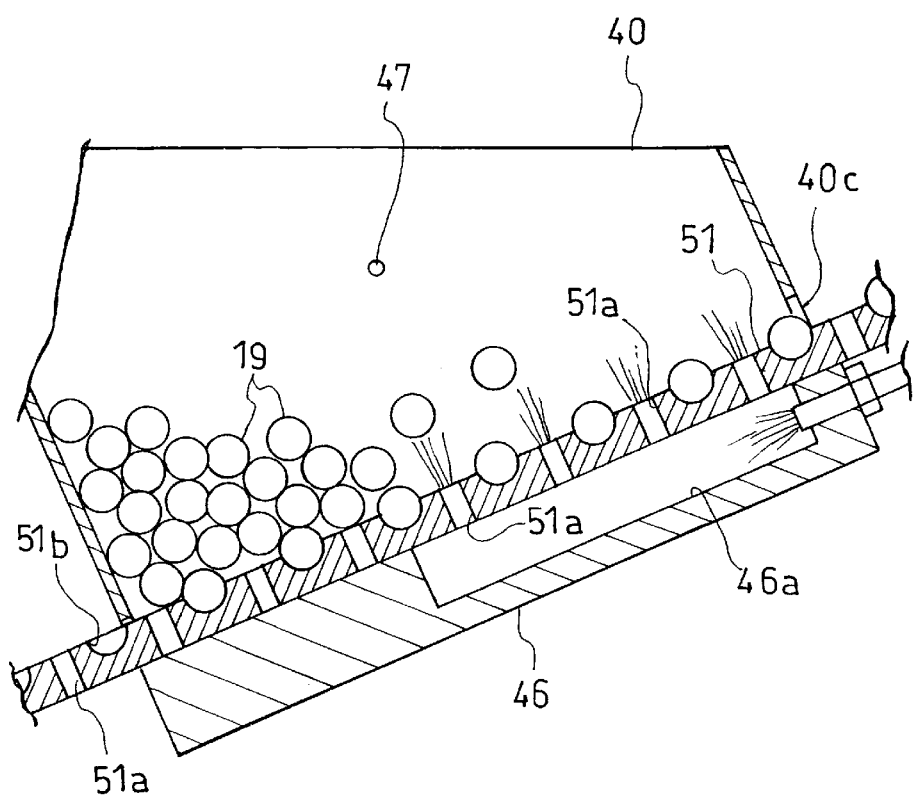
FIG. 7 is a sectional front view of a delivery hopper and a conveyer belt according to another embodiment.
Figure 8:
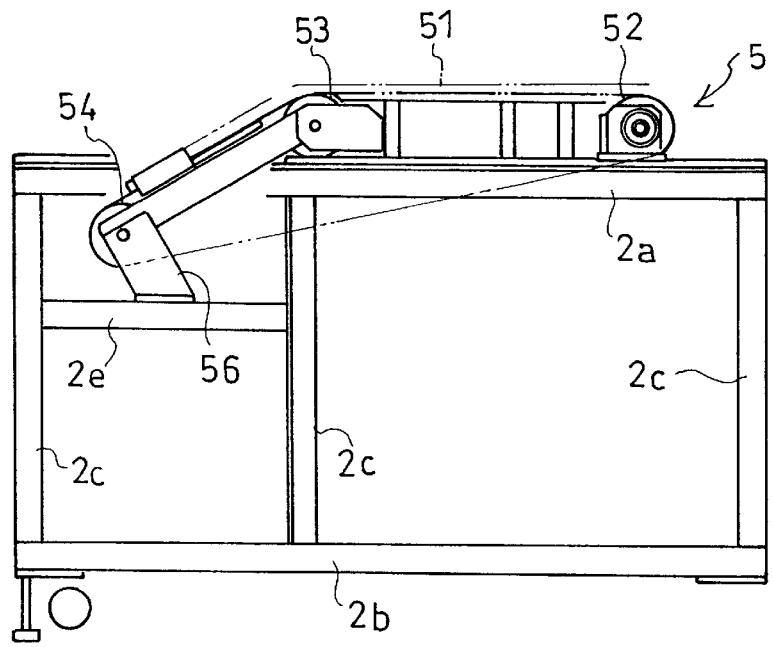
FIG. 8 is a front view of a frame and a transport device which is laid on the frame.
Figure 9:
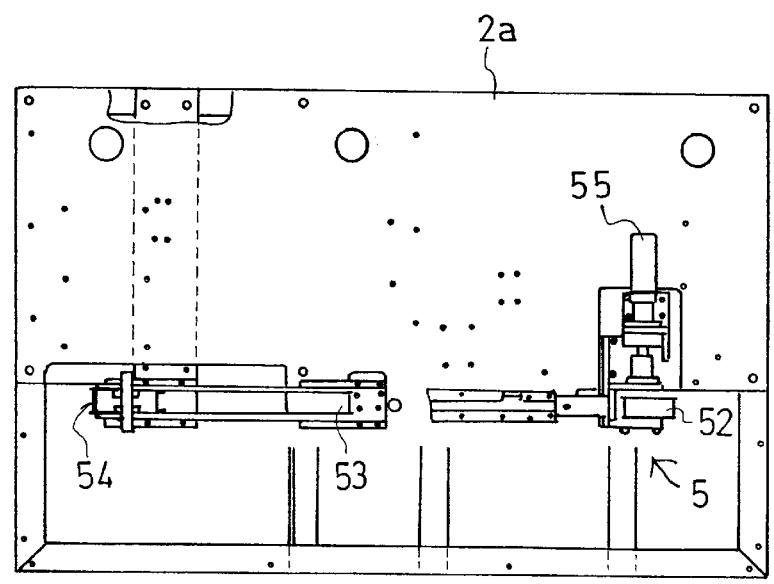
FIG. 9 is a plan view of the same.
Figure 10:
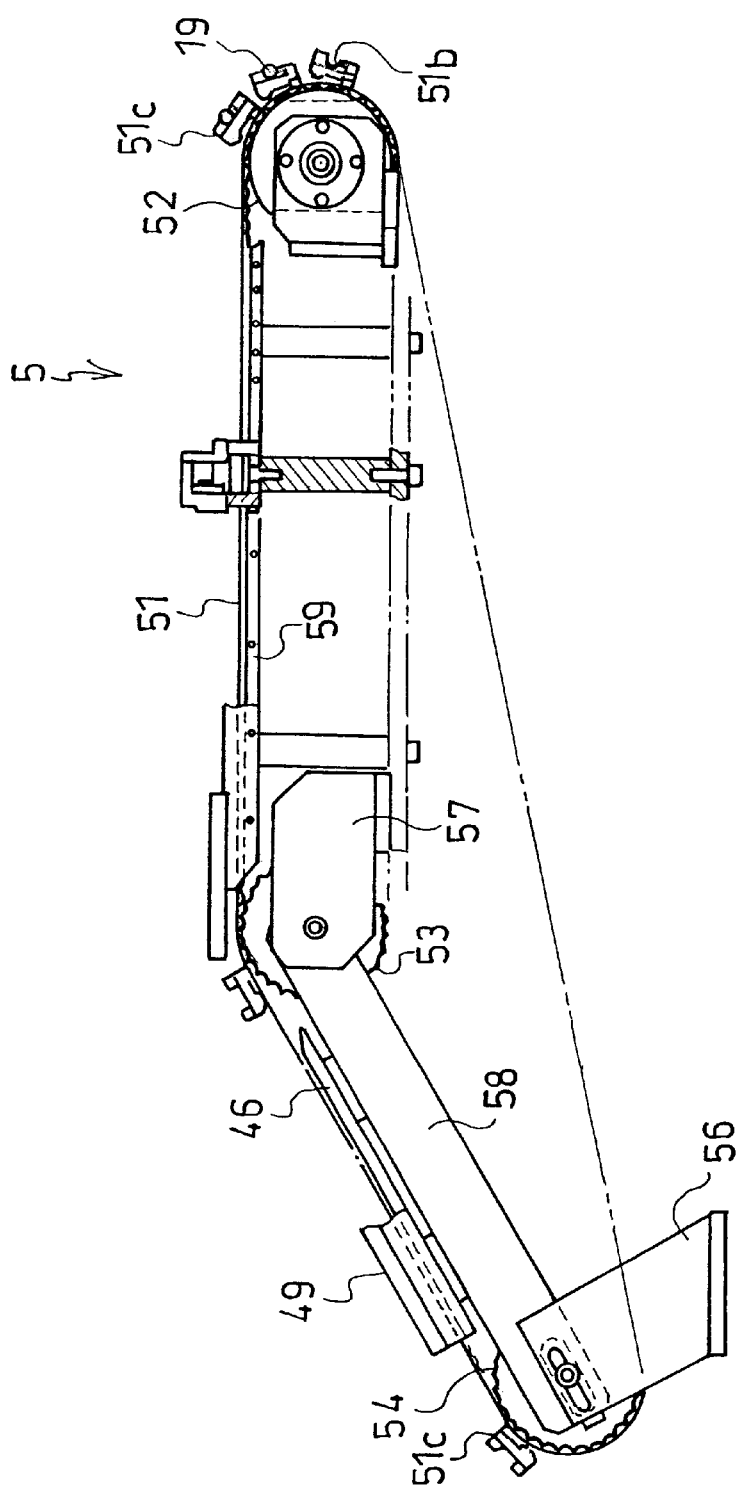
FIG. 10 is a front view partly in section of the transport device.
Figure 11:
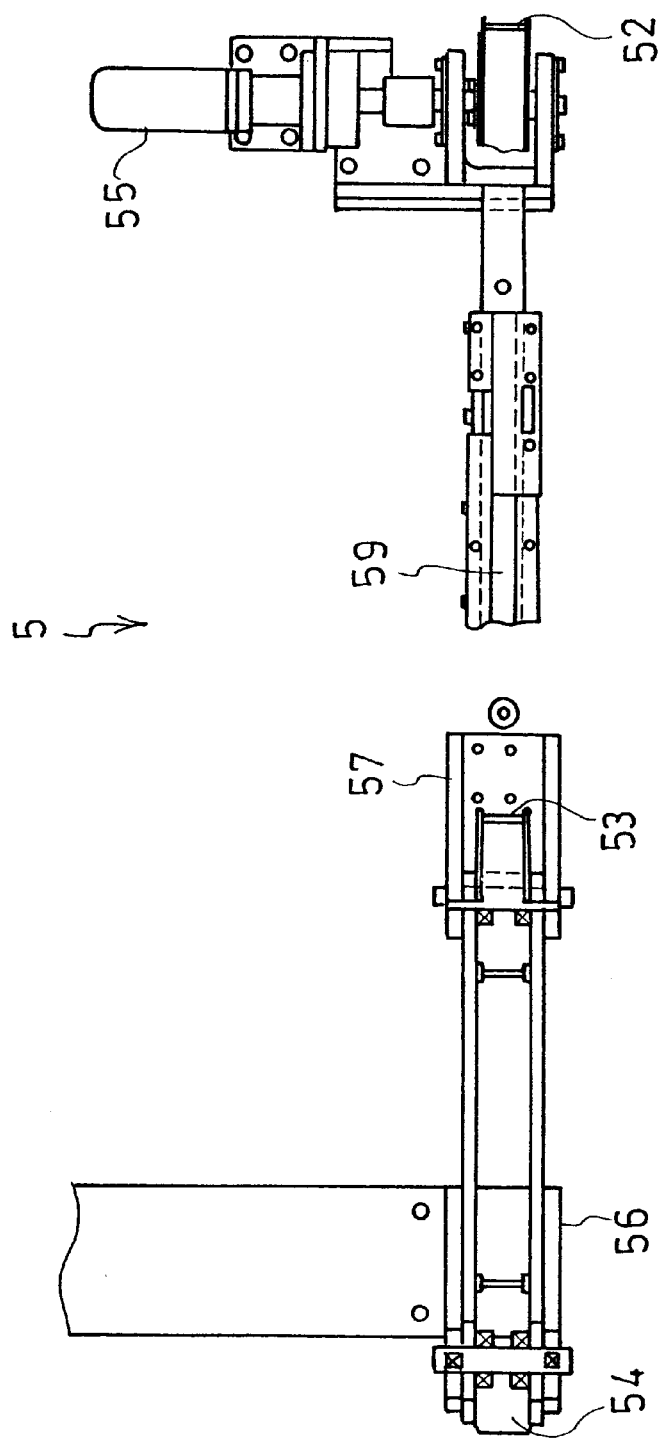
FIG. 11 is a plan view of the same.
Figure 12:
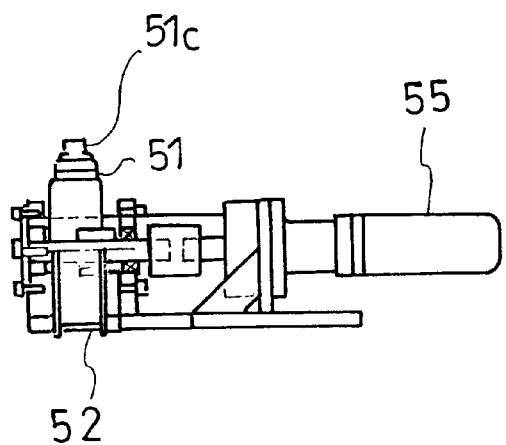
FIG. 12 is a side view of the same.

Therefore, as shown in FIG. 7, a lubricant diffuser 47 may be disposed on a side face of the delivery hopper 40. Lubricant composed of silicone oil, water, etc. is blown from the lubricant diffuser 47 and mixed with the gel covering seed 19, thereby preventing the adhesion among the gel covering seed 19. Alternatively, the inside of the delivery hopper 40 may be full of lubricant in the state of fog.

The transport device 5 will now be explained in accordance with FIGS. 8–12.

The transport device 5 conveys the gel covering seed 19 from the delivery device 4 to the accepted-product extractor 9. In the transport device 5, a drive pulley 52, an idler pulley 53, and a tension pulley 54 are arranged so as to form a triangle together. The conveyor belt 51 constituted by an endless strap is wound around these pulleys 52, 53 and 54. On the top of upper frame portion 2a, the drive pulley 52 and the idler pulley 53 are rotatably supported on respective shafts oriented in the fro-and-rear direction. A drive motor 55 is fixed on the upper frame portion 2a behind the drive pulley 52 so as to drive the drive pulley 52. The drive motor is constituted by a servomotor etc., and electrically connected to the controller 20 for controlling its rotation.

The tension pulley 54 is rotatably and slidably supported by a tension base 56 fixed on a support frame 2e laid between the stanchions 2c. The tension of the conveyor belt 51 is adjusted by the slide of the tension pulley 54 in the tension base 56.

The idler pulley 53 is rotatably supported with an idler base 57 fixed on the upper frame portion 2a. The delivery base 58 is extended aslant between the idler base 57 and the tension base 56. In order to guide the conveyor belt 51, the delivery rail 46 is fixed on the delivery base 58 in parallel. Belt guides 49 are fixed to the front and rear sides of the delivery rail 46. Both the belt guides 49 are fixed to the lower portion of the delivery hopper 40 so as to prevent the gel covering seed 19 from leaking from the gap between the delivery hopper 40 and the delivery rail 46.

The detent recesses 51b may be directly formed in the conveyor belt 51 itself as shown in FIG. 7. Alternatively, in the embodiment shown in FIG. 10, a plurality of seed cups 51c formed at their top faces with the respective detent recesses 51b are attached to the outside surface of the conveyor belt 51. The detent recess 51b corresponds in size to the gel covering seed 19 to be inspected. According to change of the kind or size of gel covering seed 19 serving as subjects of inspection, the conveyor belt 51 may be interchanged, or the gel cups 51c detachably attached to the conveyor belt 51 may be renewed while the conveyor belt 51 remains.

The conveyor belt 51 is stretched in the right-and-left horizontal direction between the drive pulley 52 and the idler pulley 53. This horizontally moving portion of the conveyor belt 51 is guided not to slacken by a conveyor rail 59 erected on the upper frame portion 2a. The discrimination device 6 and the defective product reject device 7 are arranged on a side of the conveyance rail 59.

Figure 13:
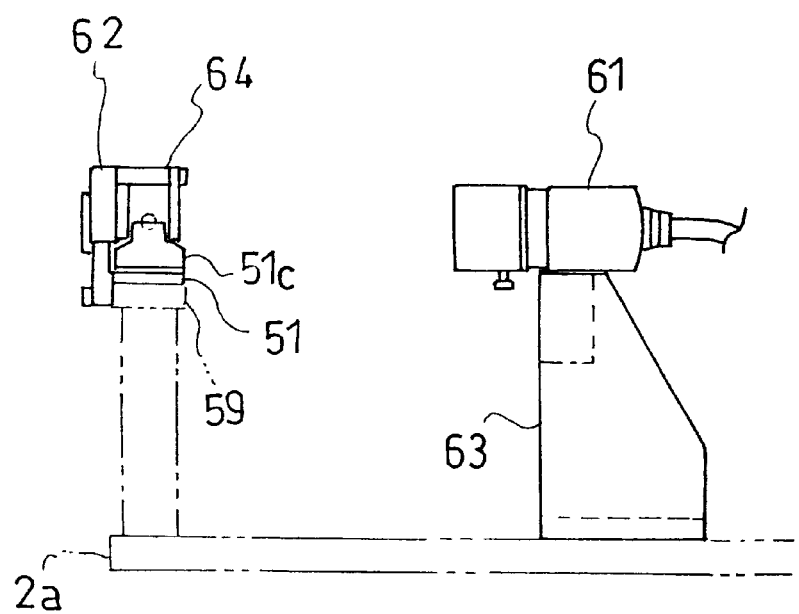
FIG. 13 is a side view of a discrimination device.

The discrimination device 6 will be explained in accordance with FIG. 13 and others. The discrimination device 6 is provided with the camera 61 comprising a CCD or so on and the luminaire 62, which are arranged face to face on both sides of the conveyor belt 51. The camera 61 and the luminaire 62 are electrically connected to the controller 20 respectively, and the camera 61 is fixed on a support frame 63 erected on the upper frame portion 2a. When each gel covering seed 19 laid on the conveyor belt 51 passes through between the camera 61 and the luminaire 62, it is judged by taking a photograph with the camera 61 whether the gel covering seed 19 is an accepted product or not.

The manner for judging acceptance or rejection of the gel covering seed 19 by use of the discrimination device 6 is not to analyze wave length of the light which appears in an reflected image of the gel covering seed 19 as usual but to analyze lightness of the shadow of the gel and the seed which appears in the image as the result of the light permeating the gel covering seed 19. This manner will now be explained in full detail.

Figure 20:
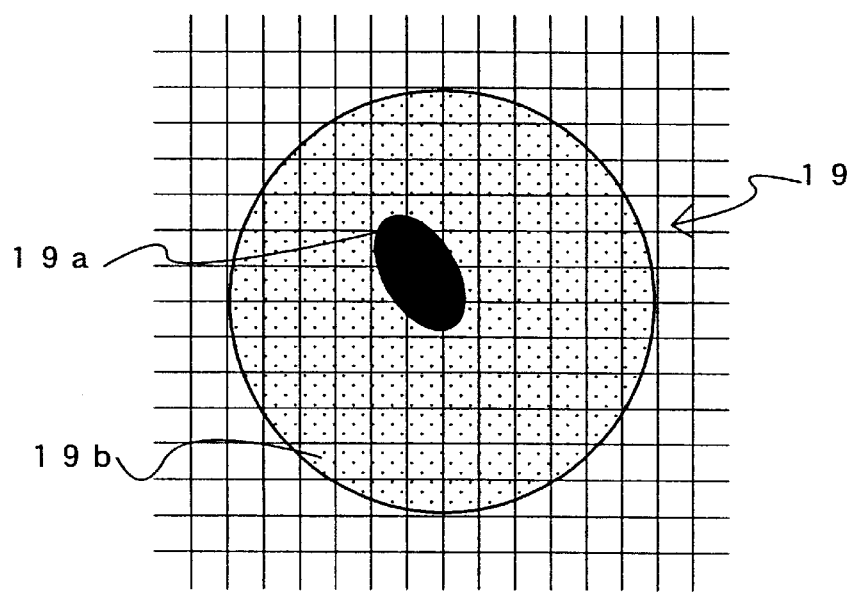
FIG. 20 is a view showing an image taken with the camera in the discrimination device.

The luminaire 62 arranged behind the passing gel covering seed 19 on the conveyor belt 51 (oppositely to the camera 61) emits light toward the camera 61. The light emitted from the luminaire 62 permeates the passing gel covering seed 19 and is projected onto the camera 61, thereby making an image as shown in FIG. 20 therein. The gel covering seed 19 is made by covering a seed 19a in gel 19b. In the photography screen of the camera 61, the gel 19b appears as a light shadow because the gel 19b is translucent so as to limit the light permeating it. A bright space illuminated by the luminaire 62 appears around the gel 19b so that the difference of lightness between the bright space and the shadow of the gel 19b defines the contour of the gel 19b. The seed 19a in the gel 19b appears as a deep shadow in the light shadow of the gel 19b because the seed 19a does not allow the light to permeate.

The discrimination device 6 calculates the area of the shadow of the seed 19a the gel 19b, which appears in the photography image of the camera 61, so as to discriminate whether the gel covering seed 19 is an accepted product or a defective product. In this regard, the tolerance zone of the area of the shadow of seed 19a, which appears in the photography image when one grain of the seed 10a is normally enclosed in each gel 19b, is previously established. If the area of the shadow of seed 19a calculated based on the photography image is smaller than the tolerance zone, the gel covering seed 19 is recognized to be a defective product by the reason that the seed 19a does not exist in the gel 19b, or the seed 19a is chipped. Conversely, if the calculated area is larger than the area of the tolerance zone, the gel covering seed 19 is also recognized to be a defective product by the reason that two or more grains of the seed 19a may be enclosed in each gel 19b.

Suppose that it is considered that the gel covering seed 19 which contains seeds 19a of two or more predetermined numbers in gel 19b is normal. The tolerance zone is established so that, when the calculated area is smaller than the area of the tolerance zone, the number of the seed 19a in each gel 19b may be recognized to be under the predetermined number, and that, when the calculated area exceeds the area of the tolerance zone, the number of the seed 19a in each gel 19b may be recognized to exceed the predetermined number. Thus, the acceptance or rejection of each gel covering seed 19 is judged by comparing the calculated area with the area of the established tolerance zone.

Actually, the area of the seed 19a in this photography image is transposed to the total number of pixels reflecting the shadow of seed 19a. That is, calculating the area implies calculating the total number of pixels.

Alternatively, the judgment of the acceptance or rejection of the gel covering seed 19 by using the photography image with the camera 61 may be not based on the area of the seed 19a but based on the area ratio of the seed 19a to the gel 19b. In this case, the ratio of the total of pixels showing the seed 19a to the total of pixels showing the gel 19b is transposed to the above-mentioned area ratio in a photography image.

In the discrimination device 6, since the passage portion of the gel covering seed 19 on the conveyor belt 51 between the camera 61 and the luminaire 62 is covered with an enclosure 64 so as to shut out unnecessary light from external illumination etc., the photography image with the camera 61 becomes still clearer. The inside of the enclosure 64, the conveyor belt 51, and the circumference components are frosted, or colored in black or dark so as to be prevented from reflecting the light of the luminaire 62 irregularly.

Furthermore, in order to ensure certainly transmitted illumination without irregular reflection, red light or infrared light is irradiated from the luminaire 62. In the reflection of the gel covering seed 19 which is irradiated with such a light and reflected on the camera 62, the seed 19a and the gel 19b are discriminated by only the lightness instead of color, i.e., the depth difference of their shadows. Therefore, a color extraction sensor, a filter, etc. which are used for the approach to reflection of the gel covering seed 19 on a camera are unnecessary, and an establishment of the color of the seed to be detected is also unnecessary. When the color of gel covering seed which appears in an image thereof is analyzed like before, misjudgment may occur because of the variation of color among seeds. Such misjudgment can be canceled by the present manner.

If there is irregularly reflected light, the seed which should appear in a photography image may be hidden by the reflected light depending on the location of the seed 19a in gel 19b so as not to be recognized. According to the present manner, the transmitted illumination from the luminaire 62 through the enclosure 64 is prevented from being irregularly reflected, thereby canceling the misjudgment caused by the interaction of the irregularly reflected light entering the camera 61 and the positional deviation of the seed 19a in gel 19b. In this way, the discrimination device 6 in the inspection apparatus 1 of the present invention can judge the acceptance or rejection of the gel covering seed 19 certainly in high accuracy.

Thus, the discrimination device 6 binary-izes each gel covering seed 19 to an accepted product and a defective product based on the photography image every when each gel covering seed 19 passes the discrimination device 6. According to the binarization, it is decided which must treat the gel covering seed 19, the defective product reject device 7 located in the downstream of the discrimination device 6, or the accepted product extractor 9 located in the further downstream of the discrimination device 6.

Figure 14:
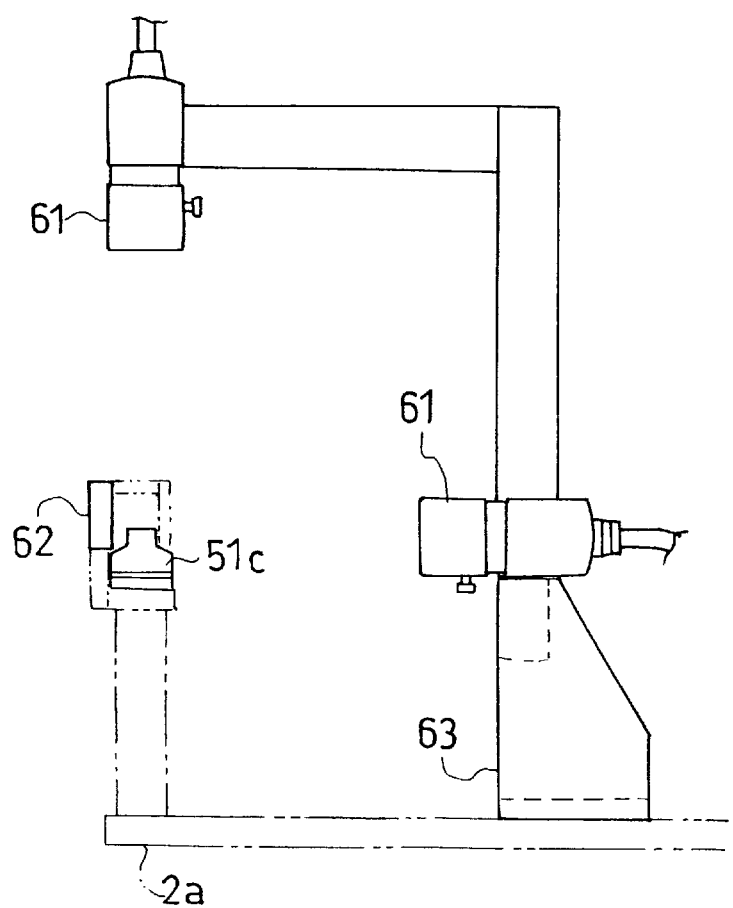
FIG. 14 is a side view of another discrimination device provided with two cameras.

In addition, if two or more seeds 19a are enclosed in gel 19b, there is a very rare case that, while they seem to be separate in one side view, they overlap and are visible to one seed 19a in another side view. Then, as shown in FIG. 14, two cameras 61 may be arranged in a rectangular location so that both the photography directions thereof intersect the conveyance direction of the gel covering seed 19 perpendicularly. In the embodiment of FIG. 14, one camera 61 is arranged on a side of the transport device 5, and the other camera 61 is arranged above the transport device 5. In this way, even if one camera 61 takes the state that the seeds 19a overlap in gel 19b, the other camera 61 can take the state the seeds 19 do not overlap. Therefore, the gel covering seed 19 is correctly judged to be a defective product.

In the case where two cameras 61 are arranged, one luminaire 62 may be opposed generally to both cameras 61 through the transport device 5, or alternatively, two luminaires 62 may be opposed respectively to the cameras 61 through the transport device 5. It is only an important point to form the illumination that enables both the cameras 61 to catch the light permeating the gel covering seed 19.

Moreover, the positional relation between two cameras 61 and the transport device 5 is not limited to the above-mentioned. Any positional relation may be accepted if it ensures accurate judgment. Further, three or more cameras 61 may be used so as to enhance the accuracy of judgment.

Figure 15:
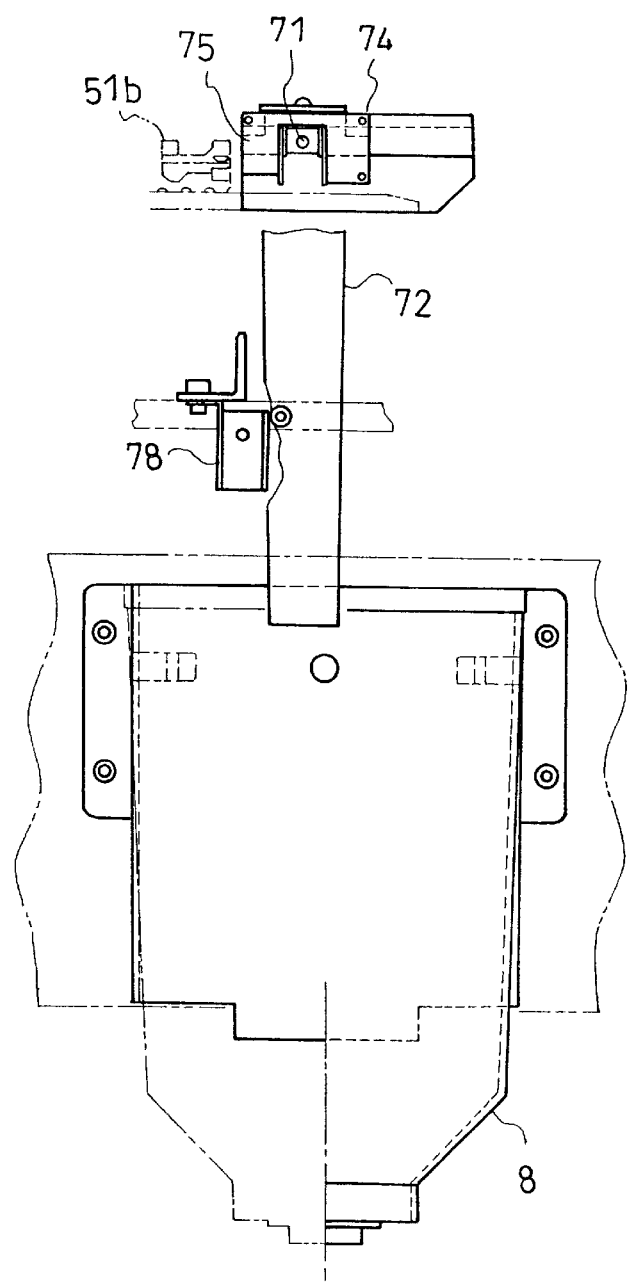
FIG. 15 is a front view of a defective product reject device.
Figure 16:
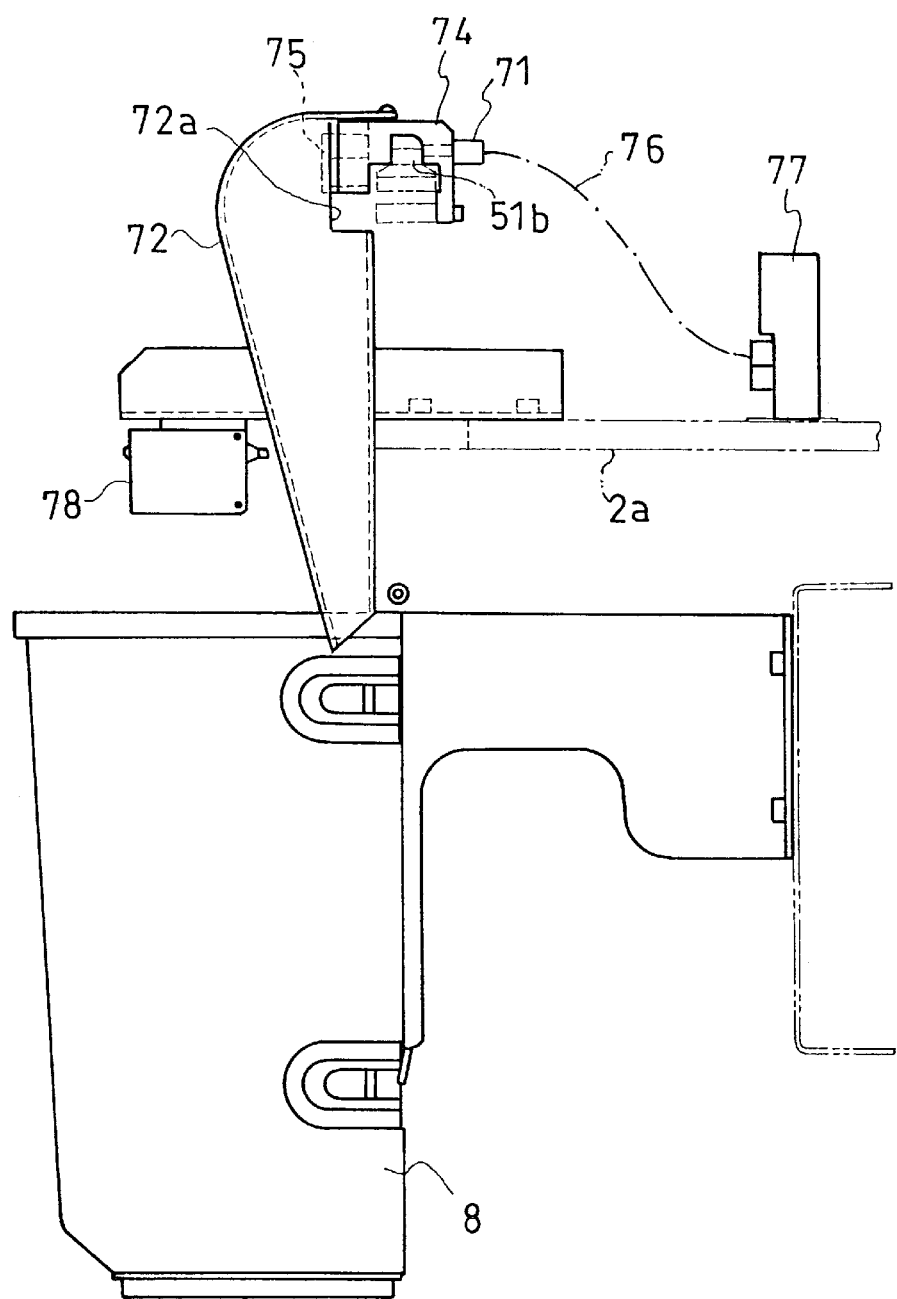
FIG. 16 is a side view of the same.

The defective product reject device 7 is arranged beside the transport device 5 at the downstream of the discrimination device 6. The defective product reject device 7 will be explained in accordance with FIGS. 15 and 16.

The defective product reject device 7 comprises an air nozzle 71, a chute 72, and a hopper 73. The air nozzle 71 is arranged on one side of the passage of gel covering seed 19 on the transport device 5, and the chute 72 on the other side. In this embodiment, the chute 72 is arranged in front of the transport device 5, and the air nozzle 71 is arranged behind the transport device 5. The chute 72 is formed at the upper rear surface thereof with an inlet port 72a, which faces a diffuser of the air nozzle 71. The air nozzle 71 is fixed to a reject ion block 74. A passage sensor 75 constituted by a photoelectric sensor etc., and an upper portion of the chute 72 are fixed to the rejection block 74. As apparent when viewed in side, the rejection block 74 is formed at the lower portion thereof with a recess for passing the detent recesses 51b of the conveyor belt 51. A defective product box 8 is arranged under the chute 72 so as to communicate with the chute 72.

The air nozzle 71 is connected to an electromagnetic valve 77 through a hose 76, and the electromagnetic valve 77 is connected to a compressor (not shown). The electromagnetic valve 77 and the chute 72 are fixed on the upper frame portion 2a, and the solenoid of the electromagnetic valve 77 is electrically connected to the controller 20. Furthermore, the passage sensor 75 electrically connected to the controller 20 is provided to detect the gel covering seed 19 just before passing the defective product reject device 7. Suppose that the gel covering seed 19 is judged to be a defective product by the discrimination device 6 in the upstream of the defective product reject device 7 and is detected by the passage sensor 75. On base of the detection by the passage sensor 75, at the time of the defective product passing through the front of the air nozzle 71, the air nozzle 71 blows off air, thereby blowing away the defective product into the chute 72.

A fall sensor 78 constituted by a photoelectric sensor etc. for detecting fall of the gel covering seed 19 as a defective product is arranged in the chute 72. When the fall sensor 78 detects the fall of the defective product, removal of the defective product from the transport device 5 is confirmed.

The defective product box 8 is detachably attached onto the front face of the frame 2. When the defective product box 8 becomes full of defective products, the defective product box 8 can be detached easily so as to eject the defective products therefrom or to be replaced with a new defective product receipt box 8.

Figure 17:
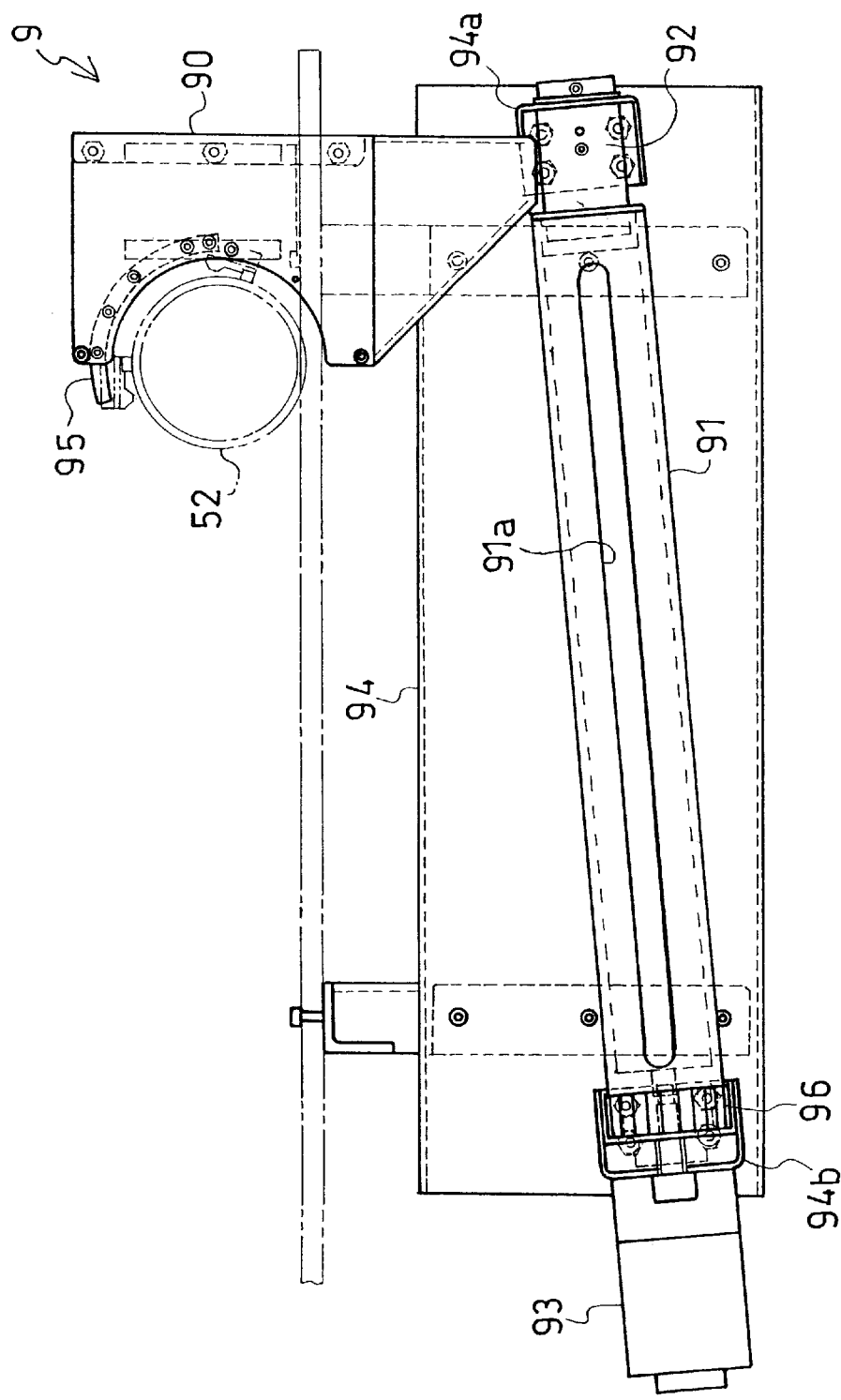
FIG. 17 is a front view of an accepted product extractor.
Figure 18:
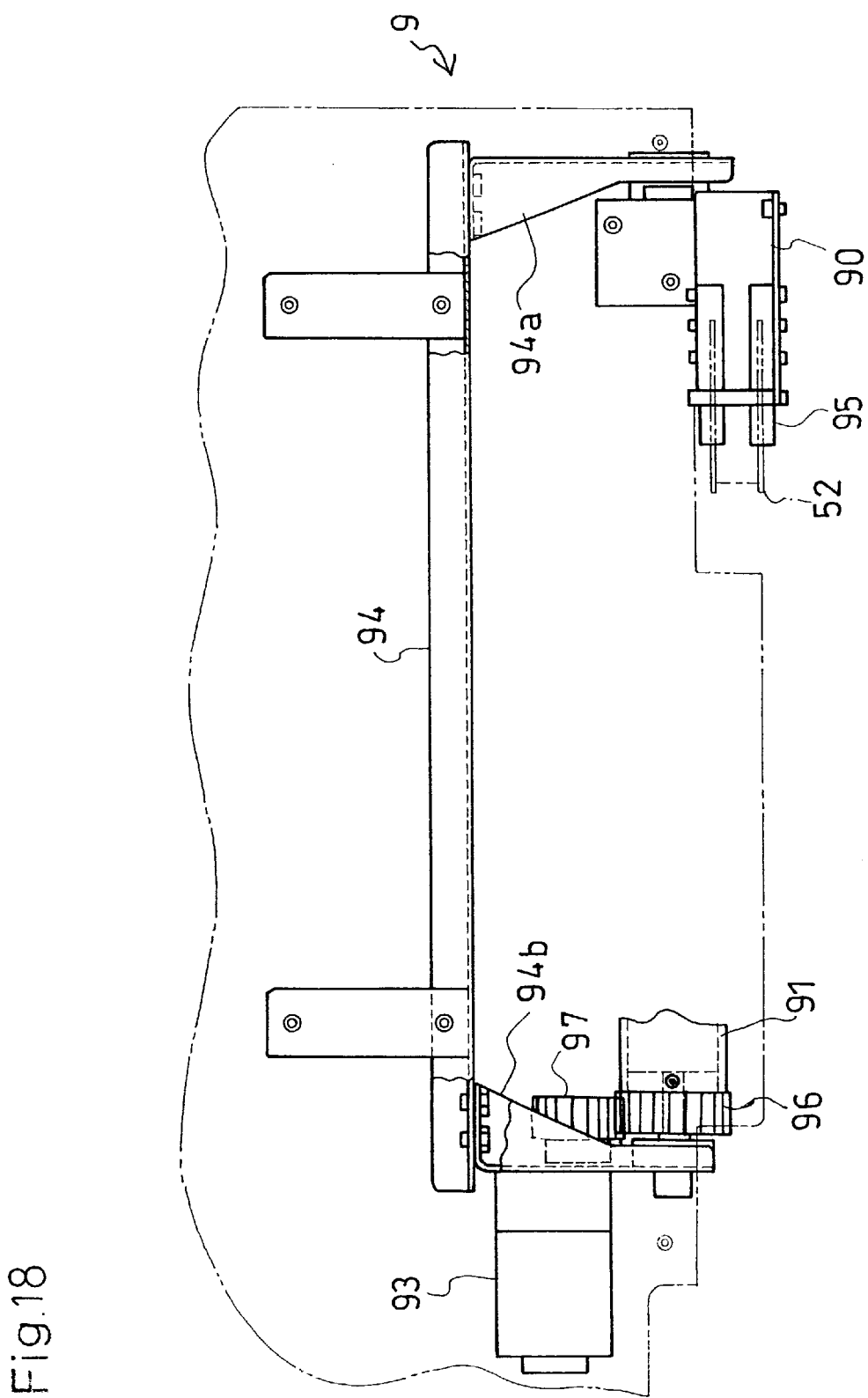
FIG. 18 is a plan view of the same.
Figure 19:
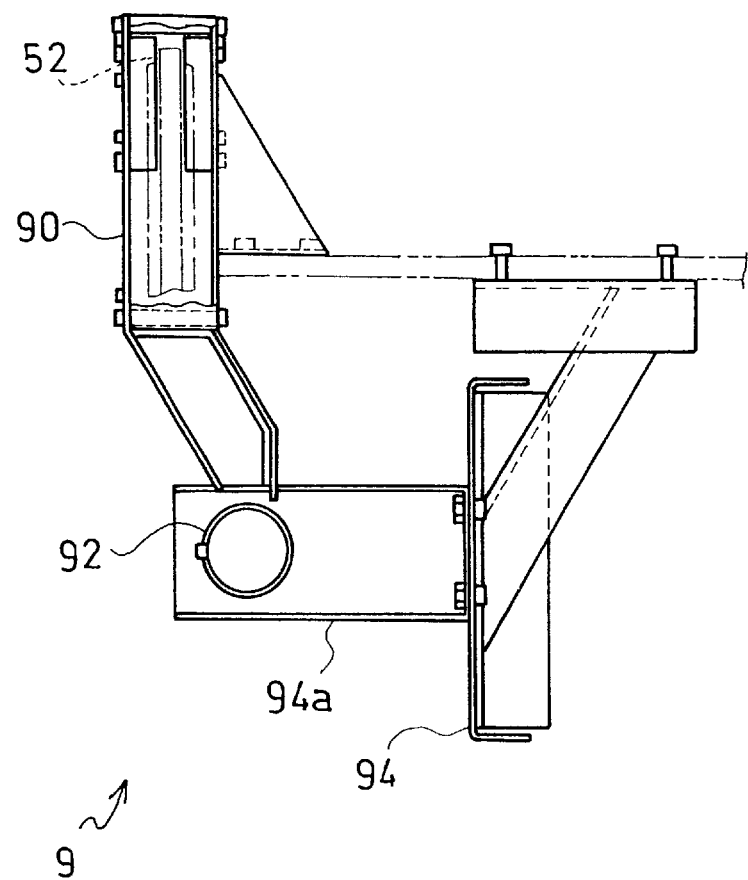
FIG. 19 is a side view of the same.

The accepted product extractor 9 is arranged under the termination of the transport device 5, and the accepted product box 10 is arranged under the accepted product extractor 9. These will be explained in accordance with FIGS. 17, 18, and 19.

The accepted product extractor 9 comprises a guide enclosure 90, a distribution cylinder 91, and a motor 93 for the rotation drive of the distribution cylinder 91. These members 90, 91 and 93 are supported by an attachment frame 94 fixed to the upper frame portion 2a of the frame 2 in the shape of lower part extension.

The guide enclosure 90 is arranged so as to cover the posterior (right-hand side of the inspection apparatus 1) of the approximate conveyance direction of the drive pulley 52 arranged at the conveyance termination of the transport device 5. A guide rail 95 is arranged along an upper portion of the guide enclosure 90 so as to guide both sides of the conveyor belt 51, thereby surely introducing each gel covering seed 19 on the conveyor belt 51 into the guide enclosure 90. The guide enclosure 90 is cylindrically extended downward so as to bring the lower end thereof into communication with the entrance port 92 of the distribution cylinder 91. Additionally, an air nozzle may be arranged above the guide enclosure 90 so as to blow off the gel covering seed 19 downward in the guide enclosure 90, thereby further surely casting the gel covering seed 19 into the guide enclosure 90.

The entrance port 92 is formed in a shape of tube, and is fixed to a bracket 94a protruding forward from the attachment frame 94. The right end of the distribution cylinder 91 rotatably fits the entrance port 92, and the other end (left end) of the distribution cylinder 91 is rotatably supported by a support portion 94b protruding forward from the attachment frame 94. The distribution cylinder 91 is arranged in the shape of an up-and-down inclination so that the entrance port 92 side may become higher. The peripheral surface of the distribution cylinder 91 is penetrated outside from inside by the slot 91a in parallel to the axial center of the distribution cylinder 91. The width of the slot 91a is set to allow the gel covering seed 19 to pass therethrough.

The other end (the lower end) of the distribution cylinder 91 are closed, and on the peripheral edge thereof, a gear 96 is fixed (or formed). The gear 96 engages with a gear 97, which is fixed on an output shaft of a motor 93 fixed to the support portion 94b, so that the distribution cylinder 91 is rotated by the drive of the motor 93. Alternatively, the gear 96 may be provided on a boss rotatably supporting the left end portion of the distribution cylinder 91.

The accepted product box 10 is arranged under the distribution cylinder 91.

In such a construction, the gel covering seed 19 judged to be an accepted product and conveyed by the transport device 5 falls from the end of a conveyor belt 51 while being guided into the entrance slot 92 by the guide enclosure 90, and then enter the distribution cylinder 91 while rolling. The rotation drive of the distribution cylinder 91 is carried out by the drive of the motor 93 through the gears 96 and 97. Due to the rotation and the inclination of the distribution cylinder 91, the gel covering seed 19 spirally roll within the distribution cylinder 91 so as to fall toward the lower end of the distribution cylinder 91. Every just when the slot 91*a* comes to the bottom of the revolving distribution cylinder 91, the gel covering seed 19 fall to the accepted product box 10 through the slot 91*a*. Therefore, by making the time for the gel covering seed 19 falling while rolling as far as the length of the slot 91*a* of the distribution cylinder 91 substantially coincide with the time for one rot at ion of the distribution cylinder 91, the gel covering seed 19 continuously ejected from the transport device 5 can be dropped from the slot 91*a* into the accepted product box 10 equally in the longitudinal direction of the slot 91*a*.

The distribution cylinder 91 distributes the gel covering seed 19 into the accepted product box 10 equally in the longitudinal direction of the distribution cylinder 91. When the gel covering seed 19 are accumulated excessively in the accepted product box 10, downwardly accumulated gel covering seed 19 are pressed to be deformed or damaged because of the weight of upwardly accumulated gel covering seed 19. Therefore, the accepted product box 10 must be exchanged frequently. Furthermore, if the distribution of gel covering seed 19 into the accepted product box 10 is eccentric, the gel covering seed 19 are accumulated high at a certain position in the accepted product box 10 earlier than those at the other position therein, thereby requiring the accepted product box 10 to be interchanged further frequently. However, since the accumulation of gel covering seed 19 in the accepted product box 10 is substantially equalized by the approximately equal distribution of gel covering seed 19 from the distribution cylinder 91, the interchange frequency of the accepted product box 10 can be reduced.

Although the invention has been described in its preferred form with a certain degree of particularity, it is understood that the present disclosure of the preferred form has been changed in the details of construction and the combination and arrangement of parts may be resorted to without departing from the spirit and the scope of the invention as hereinafter claimed.

What is claimed is:

1. A gel-covered seed inspection apparatus comprising;
   a feeder in which gel-covered seeds are accumulated;
   a delivery device which successively lets out a predetermined number of the gel-covered seeds supplied thereto at a constant rate from the feeder;
   a transport device which conveys the gel-covered seeds let out by the delivery device in a line;
   a discrimination device which judges whether each gel-covered seed on the transport device is acceptable or defective, said discrimination device comprising (i) a light source for emitting a spot light against each gel-covered seed on the transport device to produce a shadow of said gel-covered seed, and (ii) a camera adapted to determine the area of the shadow of each gel-covered seed, wherein gel-covered seeds having a shadow having an area outside a predetermined-area range are judged to be defective, whereas gel-covered seeds having a shadow having an area within the predetermined-area range are judged to be acceptable;
   a defective product reject device which rejects the gel-covered seeds judged to be defective; and
   an accepted product box which receives the gel-covered seeds judged to be acceptable.

2. The gel-covered seed inspection apparatus according to claim 1, wherein said light source and said camera are arranged face to face on both sides of said transport device.

3. The gel-covered seed inspection apparatus according to claim 1, wherein a perimeter of said light source and of a photography range with said camera is covered with an enclosure.

4. The gel-covered seed inspection apparatus according to claim 3, wherein the inside of said enclosure is black.

5. The gel-covered seed inspection apparatus according to claim 1, said accepted product extractor comprising a cylinder member and a rotation driver, wherein a peripheral surface of the cylinder member is penetrated inside-and-outside with a slot in parallel to the axial center of the cylinder member while an entrance slot for accepted products is provided on an end portion of the cylinder member, wherein the cylinder member is arranged in up-and-down slant so that an entrance port of the cylinder member turns to the upper part, and wherein the cylinder member ejects the accepted products introduced from the entrance port through the slot into said accepted product box while the cylinder member revolving with the rotation driver.

6. The gel-covered seed inspection apparatus according to claim 1, wherein said discrimination device is provided with two of said cameras which are arranged in a rectangular location, and wherein the cameras are arranged so that both photography directions of the cameras intersect the conveyance direction of the gel-covered seeds perpendicularly.

7. A gel-covered seed inspection apparatus comprising;
   a feeder in which gel-covered seeds are accumulated;
   a delivery device which successively lets out a predetermined number of the gel-covered seeds supplied thereto at a constant rate from the feeder;
   a transport device which conveys the gel-covered seeds let out by the delivery device in a line;
   a discrimination device which judges acceptance or rejection of gel-covered seeds on the transport device;
   a defective product reject device which rejects gel-covered seeds judged to be a defective product; and
   an accepted product extractor which takes out gel-covered seeds judged to be an accepted product into an accepted product box,
   wherein said discrimination device is provided with a camera and a luminaire which are arranged face to face on both sides of said transport device, wherein the discrimination device inspects the seeds by taking permeation reflection of the gel-covered seeds with the camera by light which the luminaire emits, wherein said discrimination device calculates an area of a shadow of the seeds in the gel-covered seeds which appears in said permeation reflection taken with said camera, and wherein the acceptance or rejection of gel-covered seeds is judged by comparing the calculated area with a predetermined area.

8. A gel-covered seed inspection apparatus comprising:
   a feeder for receiving and feeding gel-covered seeds;
   a first conveyer for receiving the gel-covered seeds fed from the feeder and discharging the gel-covered seeds at a rate to constantly discharge multiple gel-covered seeds;
   a second conveyer for receiving the gel-covered seeds from the first conveyer and discharging the gel-covered seeds in one line;
   an inline conveying path on which the lined gel-covered seeds from the second conveyer move;
   a detector for detecting defective gel-covered seeds moving on the inline conveying path, said detector comprising a light source for emitting a spot light against each gel-covered seed on the inline conveying oath to produce a shadow of said gel-covered seed, and a camera device adapted to determine the area of the shadow of each gel-covered seed, wherein gel-covered seeds having a shadow having an area outside a predetermined-area range are judged to be defective;

a rejecting device for rejecting the defective gel-covered seeds detected by the detector; and a collection device for collecting gel-covered seeds which have not been detected by the detector.

9. A gel-covered seed inspection comprising:

a feeder in which gel-covered seeds are accumulated;

a delivery device which successively lets out a predetermined number of the gel-covered seeds supplied thereto at a constant rate from the feeder;

a transport device which conveys the gel-covered seeds let out by the delivery device in a line;

a discrimination device which judges acceptance or rejection of gel-covered seeds during conveying the gel-covered seeds by the transport device;

a defective product reject device which rejects gel-covered seeds judged to be a defective product; and an accepted product extractor which takes out gel-covered seeds judged to be an accepted product into an accepted product box, wherein said discrimination device is provided with a camera and a luminaire which are arranged face to face on both sides of said transport device, wherein the discrimination device inspects the seeds by taking permeation reflection of the gel-covered seeds with the camera by light which the luminaire emits, wherein a perimeter of said luminaire and of a photography range with said camera is covered with an enclosure, and wherein the inside of said enclosure is black.

10. A gel-covered seed inspection apparatus comprising:

a feeder in which gel-covered seeds are accumulated;

a delivery device which successively lets out a predetermined number of the gel-covered seeds supplied thereto at a constant rate from the feeder;

a transport device which conveys the gel-covered seeds let out by the delivery device in a line;

a discrimination device which judges acceptance or rejection of gel-covered seeds during conveying the gel-covered seeds by the transport device;

a defective product reject device which rejects gel-covered seeds judged to be a defective product; and an accepted product extractor which takes out gel-covered seeds judged to be an accepted product into an accepted product box, wherein said accepted product extractor comprises a cylinder member and a rotation driver, wherein a peripheral surface of the cylinder member is penetrated inside-and-outside with a slot in parallel to the axial center of the cylinder member while an entrance slot for accepted products is provided on an end portion of the cylinder member, wherein the cylinder member is arranged in up-and-down slant so that an entrance port of the cylinder member turns to the upper part, and wherein the cylinder member ejects the accepted products introduced from the entrance port through the slot into said accepted product box while the cylinder member revolving with the rotation driver.

11. A method of producing a batch of gel-covered seeds comprising:

accumulating gel-covered seeds into a feeder;

successively letting out a predetermined number of gel-covered seeds from the feeder;

transporting the gel-covered seeds away from the feeder;

emitting a spotlight against each gel-covered seed being transported;

producing a shadow of each gel-covered seed lit by the spot light;

calculating the area of the shadow of each gel-covered seed;

accepting gel-covered seeds having an area within a predetermined-area range and rejecting gel-covered seeds having an area other than said predetermined-area range; and accumulating said batch of gel-covered seeds from the accepted gel-covered seeds.

* * * * *